US010821136B2

(12) United States Patent
Ando et al.

(10) Patent No.: US 10,821,136 B2
(45) Date of Patent: Nov. 3, 2020

(54) BONE FORMATION PROMOTER

(71) Applicants: NATIONAL UNIVERSITY CORPORATION TOAKI NATIONAL HIGHER EDUCATION AND RESEARCH SYSTEM, Nagoya (JP); MENICON CO., LTD., Nagoya-shi, Aichi (JP)

(72) Inventors: Kei Ando, Nagoya (JP); Naoki Ishiguro, Nagoya (JP); Shiro Imagama, Nagoya (JP); Zenya Ito, Nagoya (JP); Yasuhiro Yokoyama, Kasugai (JP); Hidenori Yokoi, Kasugai (JP); Yusuke Nagai, Nagoya (JP)

(73) Assignees: NATIONAL UNIVERSITY CORPORATION TOKAI NATIONAL HIGHER EDUCATION AND RESEARCH SYSTEM, Nagoya (JP); MENICON CO., LTD., Nagoya (JP)

( * ) Notice: Subject to any disclaimer, the term of this patent is extended or adjusted under 35 U.S.C. 154(b) by 0 days.

(21) Appl. No.: 15/317,569

(22) PCT Filed: Jun. 29, 2015

(86) PCT No.: PCT/JP2015/068683
§ 371 (c)(1),
(2) Date: Dec. 9, 2016

(87) PCT Pub. No.: WO2016/002717
PCT Pub. Date: Jan. 7, 2016

(65) Prior Publication Data
US 2017/0119825 A1 May 4, 2017

(30) Foreign Application Priority Data

Jun. 30, 2014 (JP) ................................ 2014-134730

(51) Int. Cl.
| | | |
|---|---|---|
| *A61K 35/32* | (2015.01) | |
| *A61K 35/14* | (2015.01) | |
| *A61K 38/18* | (2006.01) | |
| *C07K 17/14* | (2006.01) | |
| *A61L 31/00* | (2006.01) | |
| *A61K 38/00* | (2006.01) | |
| *A61K 38/10* | (2006.01) | |

(52) U.S. Cl.
CPC ............. *A61K 35/32* (2013.01); *A61K 35/14* (2013.01); *A61K 38/00* (2013.01); *A61K 38/10* (2013.01); *A61K 38/1875* (2013.01); *A61L 31/00* (2013.01); *C07K 17/14* (2013.01); *A61L 2430/02* (2013.01)

(58) Field of Classification Search
CPC ........ A61K 35/14; A61K 35/32; A61K 38/00; A61K 38/10; A61K 38/1875; A61L 2430/02; A61L 31/00; C07K 17/14
See application file for complete search history.

(56) References Cited

U.S. PATENT DOCUMENTS

| | | | |
|---|---|---|---|
| 7,897,163 | B2 | 3/2011 | Park et al. |
| 8,022,178 | B2 | 9/2011 | Horii et al. |
| 8,299,032 | B2 | 10/2012 | Yokoi et al. |
| 8,729,032 | B2 | 5/2014 | Nagai et al. |
| 8,951,974 | B2 | 2/2015 | Nagai et al. |
| 2007/0160681 | A1 | 7/2007 | Park et al. |
| 2009/0162437 | A1 | 6/2009 | Horii et al. |
| 2010/0015197 | A1 | 1/2010 | Rapaport |
| 2010/0016548 | A1 | 1/2010 | Yokoi et al. |
| 2010/0317587 | A1 | 12/2010 | Chung et al. |
| 2011/0305741 | A1 | 12/2011 | Zamora et al. |
| 2012/0058066 | A1* | 3/2012 | Nagai et al. ............ A61L 15/60 424/70.1 |
| 2014/0161753 | A1 | 6/2014 | Nagai et al. |
| 2014/0286888 | A1 | 9/2014 | Nagai et al. |
| 2015/0125611 | A1 | 5/2015 | Nagai et al. |
| 2015/0175663 | A1 | 6/2015 | Yokoi et al. |
| 2015/0315242 | A1 | 11/2015 | Nagai et al. |

FOREIGN PATENT DOCUMENTS

| | | |
|---|---|---|
| CN | 100594947 C | 3/2010 |
| CN | 102348717 A | 2/2012 |
| JP | 2006-068250 A | 3/2006 |
| JP | 2010-504972 A | 2/2010 |
| JP | 2012-082180 A | 4/2012 |

(Continued)

OTHER PUBLICATIONS

Yusuke Nagai , The mechanical stimulation of cells in 3D culture within a self-assembling peptide hydrogel, Biomaterials 33 (2012) 1044e1051.*

Jorge Arenaz-Búa, A comparative study of platelet-rich plasma, hydroxyapatite, demineralized bone matrix and autologous bone to promote bone regeneration after mandibular impacted third molar extraction, Med Oral Patol Oral Cir Bucal. May 1, 2010;15 (3):e483-9.*

Ryoko Yoshimi, Self-Assembling Peptide Nanofiber Scaffolds, Platelet-Rich Plasma, and Mesenchymal Stem Cells for Injectable Bone Regeneration With Tissue Engineering, J Craniofac Surg 2009;20: 1523Y1530).*

(Continued)

*Primary Examiner* — James H Alstrum-Acevedo
*Assistant Examiner* — Erinne R Dabkowski
(74) *Attorney, Agent, or Firm* — Oliff PLC

(57) ABSTRACT

The present invention provides a bone formation promoter having high biological safety and capable of promoting bone formation. The bone formation promoter of the present invention includes a self-assembling peptide capable of forming a β-sheet structure in an aqueous solution having a neutral pH; and a bone chip. A sum of charges of amino acid residues constituting the self-assembling peptide at pH 7.0 is unequal to 0.

7 Claims, 12 Drawing Sheets
(1 of 12 Drawing Sheet(s) Filed in Color)
Specification includes a Sequence Listing.

(56) References Cited

FOREIGN PATENT DOCUMENTS

| JP | 2012-131757 A | 7/2012 |
|---|---|---|
| JP | 2015-144767 A | 8/2015 |
| WO | 2005/014615 A2 | 2/2005 |
| WO | 2007/000979 A1 | 1/2007 |
| WO | 2009/072119 A2 | 6/2009 |
| WO | 2010/103887 A1 | 9/2010 |
| WO | 2014/010721 A1 | 1/2014 |
| WO | 2014/133027 A1 | 9/2014 |

OTHER PUBLICATIONS

Tianyong Hou, A composite demineralized bone matrix e Self assembling peptide scaffold for enhancing cell and growth factor activity in bone marrow, Biomaterials 35 (2014) 5689e5699.*

Sep. 15, 2015 International Search Report issued in International Patent Application No. PCT/JP2015/068683.

Jan. 3, 2017 International Preliminary Report on Patentability issued in International Patent Application No. PCT/JP2015/068683.

Haruo Misawa et al; "PuraMatrix Facilities™ Bone Regeneration in Bone Defects of Calvaria in Mice;" Cell Transplantation; 2006; vol. 15; pp. 903-910.

Yusuke Nagai et al; "The mechanical stimulation of cells in 3D culture within a self-assembling peptide hydrogel;" Journal of Okayama Medical Association; 2014; vol. 126; pp. 7-10.

Jiro Takei; "Self-Assembling, 3-Dimensional Scaffold Peptide Hydrogel for Bone Regeneration;" Journal of the Japanese Association of Regenerative Dentistry; 2005; vol. 3; No. 1; pp. 1-11.

Yusuke Nagai et al; "The mechanical stimulation of cells in 3D culture within a self-assembling peptide hydrogel;" Biomaterials; 2012; vol. 33; No. 4; pp. 1044-1051.

Hidenori Yokoi et al; "Strategy for Designing Self-Assembling Peptides to Prepare Transparent Nanofiber Hydrogel at Neutral pH;" Journal of Nanomaterials; 2012; vol. 2012; Article ID 537262; pp. 1-9.

Amosi et al; "Acidic Peptide Hydrogel Scaffolds Enhance Calcium Phosphate Mineral Turnover Into Bone Tissue;" ACTA Biomaterialia; vol. 8; No. 7; Apr. 2012; pp. 2466-2475.

Dec. 28, 2018 Office Action issued in Chinese Patent Application No. 201580036020.7.

* cited by examiner

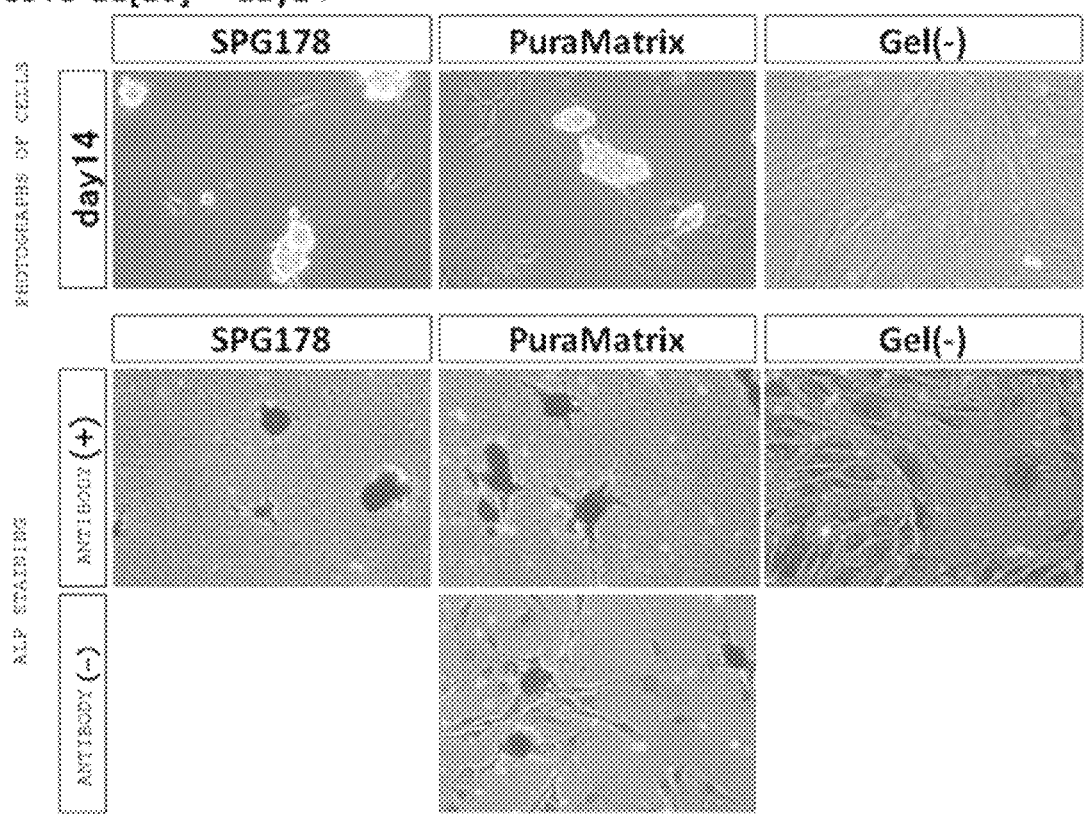

FIG. 7

|  | No. 1 | No. 2 | No. 3 | No. 4 |
|---|---|---|---|---|
| SPG178 | | | | |
| BONE REGENERATION RATE | 69.49% | 63.98% | 54.18% | 79.05% |
| PuraMatrix | | | | |
| BONE REGENERATION RATE | 29.12% | 38.72% | 17.92% | 40.42% |
| PHYSIOLOGICAL SALINE | | | | |
| BONE REGENERATION RATE | 38.39% | 50.66% | 40.67% | 47.00% |

FIG. 8

|  | No. 1 | No. 2 | No. 3 | No. 4 |
|---|---|---|---|---|
| SPG178 | | | | |
| BONE REGENERATION RATE | 69.49% | 63.98% | 54.18% | 79.05% |
| PuraMatrix | | | | |
| BONE REGENERATION RATE | 29.12% | 38.72% | 17.92% | 40.42% |
| PHYSIOLOGICAL SALINE | | | | |
| BONE REGENERATION RATE | 38.39% | 50.66% | 40.67% | 47.00% |

(a)

(b)

(c)

BONE FORMATION PROMOTER

TECHNICAL FIELD

The present invention relates to a bone formation promoter. More specifically, the present invention relates to a bone formation promoter including a self-assembling peptide and a bone chip.

BACKGROUND ART

Spine has not only a role in supporting a body against gravity but also a role in protecting the spinal cord of a central nerve. In orthopedics, particularly in a spine-related field, there are big issues about a disease that causes compression of a nerve such as the spinal cord (for example, cervical spondylotic myelopathy) and a fracture of the spine. The compression of the spinal cord requires a treatment to resect a bone that compresses the spinal cord. In general, the spine having become unstable by resection is subjected to transplantation of a bone collected from a patient himself/herself or fixation using a metal, such as a metallic bolt or plate.

In addition, a fractured bone is basically treated by reposition and fixation, and in general, a method involving fixing a bone using a metal to cause bone fusion is adopted. However, the bone fractures of the extremities require a fusion period as long as from 2 months to 3 months, and the bone fracture of the spine requires a fusion period as long as from 6 months to 1 year or more. In particular, an aged person has reduced bone strength, and hence the bone may be fractured again before completion of the bone fusion, or the metal used for fixation may be out of position. In addition, a patient with femoral neck fracture or spine fracture may be required to rest in bed, and hence may develop disuse syndrome and require care.

In recent years, various surgery methods and fixation materials have been developed to improve cure rates of fractured bones. However, such methods and materials may still cause after effects, such as delayed union (delayed bone fusion) and false joint (stopped bone fusion). In addition, for a spine surgery, more effective implants or surgery technologies to be used in spine fixation for reconstruction of the spine have been developed. However, when the technologies are applied to an aged person who has reduced bone regeneration function, bone fusion may not progress appropriately.

In recent years, as a method of promoting bone regeneration, for example, there has been tried a method of transplanting cultured cells such as osteoblasts into an affected site or placement of a cell scaffold to an affected site. As the cell scaffold, for example, an extracellular matrix as typified by gelatin and collagen has been used, but the gelatin and the collagen have a drawback of application restricted depending on, for example, the kind of an animal that supplies the materials. Meanwhile, it has been reported that bone regeneration can be promoted by administration of only a fully synthesized self-assembling peptide or by administration of a mixture of the peptide and a bone differentiation induction factor (Patent Literature 1, Patent Literature 2, Patent Literature 3, and Non Patent Literature 1). However, bone formation promoters each including a self-assembling peptide and having been reported to promote bone regeneration are hard to secure adequate strength under a neutral condition similar to a body environment.

CITATION LIST

Patent Literature

[PTL 1] JP 2012-82180 A
[PTL 2] JP 2010-504972 A
[PTL 3] WO 2007/000979 A1

Non Patent Literature

[NPL 1] Cell Transplantation, Vol. 15, p 903-910, 2006

SUMMARY OF INVENTION

Technical Problem

An object of the present invention is to provide a bone formation promoter having high biological safety and capable of promoting bone formation.

Solution to Problem

According to one aspect of the present invention, there is provided a bone formation promoter, including: a self-assembling peptide capable of forming a β-sheet structure in an aqueous solution having a neutral pH; and a bone chip, a sum of charges of amino acid residues constituting the self-assembling peptide at pH 7.0 being unequal to 0.

In one embodiment, the self-assembling peptide includes a self-assembling peptide having the following amino acid sequence:

$$a_1b_1c_1b_2a_2b_3db_4a_3b_6c_2b_6a_4 \qquad \text{Amino acid sequence:}$$

where: $a_1$ to $a_4$ each represent a basic amino acid residue; $b_1$ to $b_6$ each represent a non-charged polar amino acid residue and/or a hydrophobic amino acid residue, provided that at least five thereof each represent a hydrophobic amino acid residue; $c_1$ and $c_2$ each represent an acidic amino acid residue; and d represents a hydrophobic amino acid residue.

In one embodiment, the bone formation promoter further includes blood and/or a blood-derived component.

In one embodiment, the bone formation promoter further includes a bone morphogenetic protein.

In one embodiment, the bone formation promoter is used in combination with a retainer for a bone formation promoter.

According to another aspect of the present invention, there is provided a retainer for a bone formation promoter. The retainer for a bone formation promoter of the present invention is used together with the bone formation promoter.

In one embodiment, the retainer for a bone formation promoter is formed of a carbon-based material, an engineering resin, or a super engineering resin.

Advantageous Effects of Invention

According to the present invention, the bone formation promoter having high biological safety and capable of promoting bone formation can be provided. The bone formation promoter of the present invention includes a self-assembling peptide capable of forming a β-sheet structure in an aqueous solution having a neutral pH, and a bone chip. The bone formation promoter can form many origins of bone formation to suitably promote bone formation. Accordingly, the bone formation promoter can improve bone formation even in an aged person who has reduced bone strength and reduced bone regeneration ability. In addition, the bone formation promoter of the present invention can induce new bone formation without using cells directly involved in bone formation. Further, the self-assembling peptide to be used in the present invention forms a β-sheet structure in an aqueous solution having a neutral pH, and the sum of charges of amino acid residues constituting the self-assembling peptide at pH 7.0 is unequal to 0. Accordingly, the bone formation promoter of the present invention can exhibit adequate strength at a neutral pH similar to that of a body environment. Further, the bone formation promoter can be fixed at a desired position using an appropriate retainer, such as the retainer for a bone formation promoter of the present invention.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1C shows photographs of MC3T3-E1 cells on day 14 of culture and photographs of the cells subjected to ALP staining.

FIG. 7 shows X-ray images of mouse femurs on day 56 of the external fixation.

FIG. 8 shows CT images of mouse femurs on day 56 of the external fixation.

DESCRIPTION OF EMBODIMENTS

[A. Bone Formation Promoter]

Figure 1A:
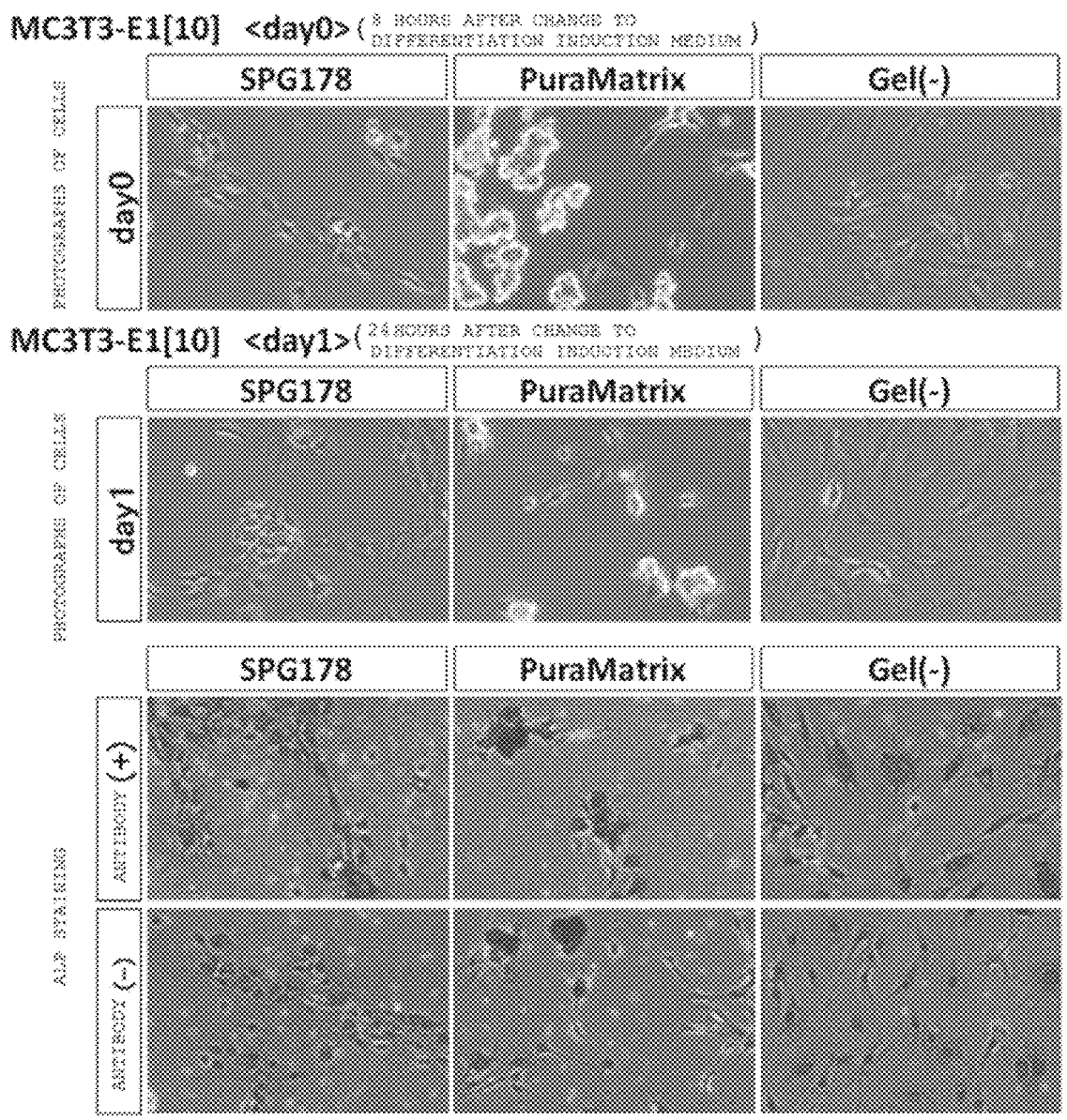
FIG. 1A shows photographs of MC3T3-E1 cells on day 0 of culture, photographs of MC3T3-E1 cells on day 1 of culture, and photographs of the cells subjected to ALP staining.
Figure 1B:
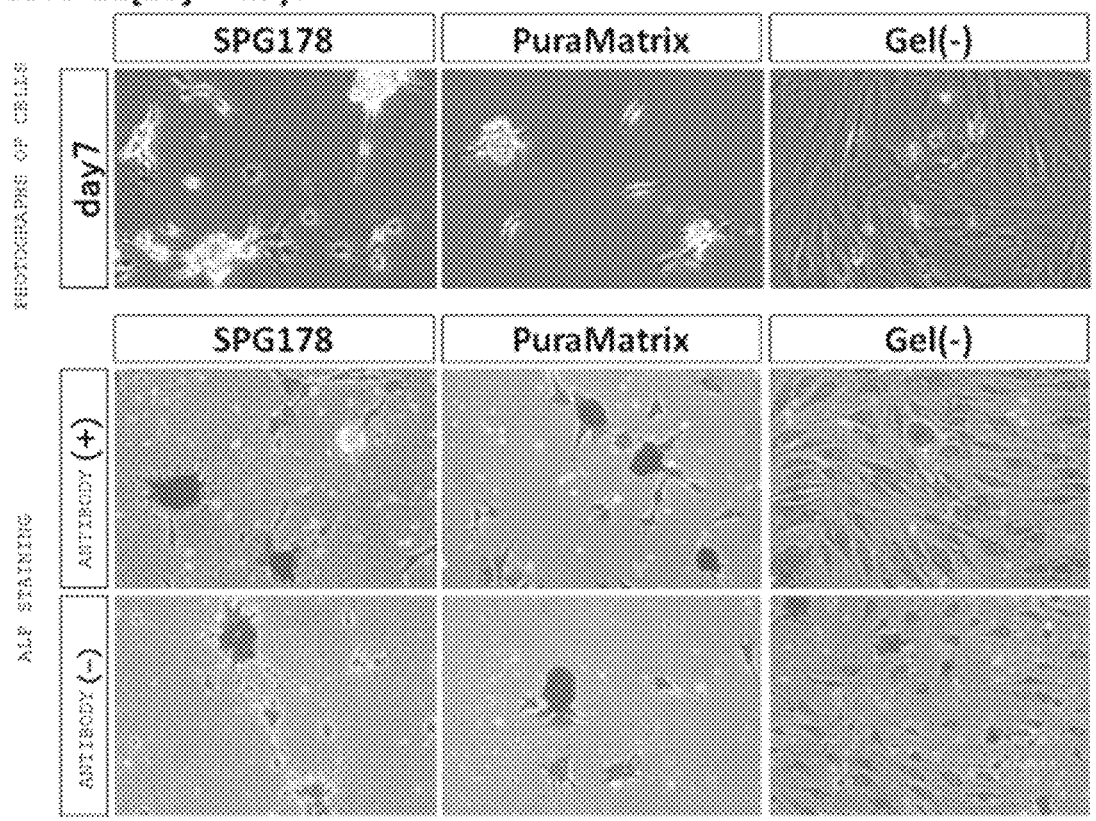
FIG. 1B shows photographs of MC3T3-E1 cells on day 7 of culture and photographs of the cells subjected to ALP staining.
Figure 1D:
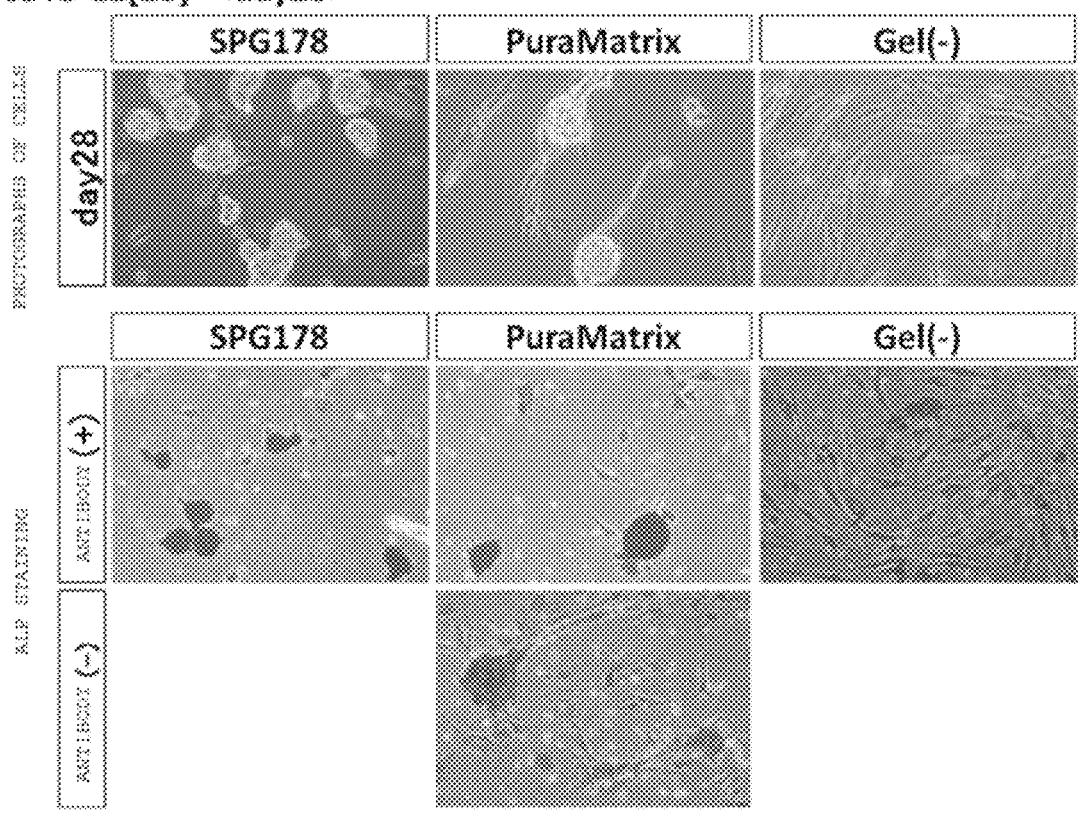
FIG. 1D shows photographs of MC3T3-E1 cells on day 28 of culture and photographs of the cells subjected to ALP staining.

A bone formation promoter of the present invention includes a self-assembling peptide capable of forming a β-sheet structure in an aqueous solution having a neutral pH, and a bone chip. The sum of charges of amino acid residues constituting the self-assembling peptide at pH 7.0 is unequal to 0. In one embodiment, the bone formation promoter of the present invention further includes blood and/or a blood-derived component. In addition, in another embodiment, the bone formation promoter of the present invention further includes a bone morphogenetic protein.

The bone formation promoter of the present invention has a storage modulus (G') at 37° C., as determined by dynamic viscoelasticity measurement using a rotational rheometer, of, for example, from 1 Pa to 5,000 Pa, preferably from 1 Pa to 4,000 Pa, more preferably from 1 Pa to 3,000 Pa. When the storage modulus falls within such range, the bone formation promoter can be used together with a retainer for a bone formation promoter of the present invention to be described later to suitably promote bone formation. The term "storage modulus" as used herein refers to a value when an angular frequency determined by frequency change measurement is 1 radian per second.

[A-1. Self-Assembling Peptide]

As the self-assembling peptide, there may be used any appropriate peptide capable of spontaneously assembling in an aqueous solution to form a gel through an interaction of peptide molecules. The self-assembling peptide to be used in the present invention can form a β-sheet structure at a neutral pH. More specifically, there may be preferably used a peptide capable of spontaneously assembling in an aqueous solution to form fibrous molecular assemblies through an interaction of peptide molecules and developing a three-dimensional network structure to form a gel through an interaction of the molecular assemblies. As the interaction of the peptide molecules, there are given, for example: an electrostatic interaction, such as hydrogen bonding, interionic interaction, or van der Waals force; and a hydrophobic interaction. The term "neutral pH (neutral region)" as used herein refers to a region ranging from pH 5.0 to pH 8.0, preferably ranging from pH 5.5 to pH 7.5, more preferably ranging from pH 6.0 to pH 7.0, even more preferably of pH 7.0.

The amino acids constituting the self-assembling peptide may be L-amino acids or D-amino acids. The amino acids are preferably L-amino acids. In addition, the amino acids may be natural amino acids or non-natural amino acids. The amino acids are preferably natural amino acids because the natural amino acids are available at low cost and peptides can be easily synthesized therefrom.

The sum of charges of amino acid residues constituting the self-assembling peptide at pH 7.0 is unequal to 0. The sum of the charges is preferably from −3 to −1 or from +1 to +3, more preferably −3, −2, +2, or +3. When positive charges and negative charges derived from side chains of amino acid residues included in the self-assembling peptide in a neutral region are not balanced as mentioned above, static attraction and repulsion suitable for formation of a gel are balanced, resulting in forming a transparent and stable gel in a neutral region.

The charges of the self-assembling peptide at different pH values may be determined by a program available on a website of PROTEIN CALCULATOR v3.4 (http://protcalc.sourceforge.net/).

As a specific example of the self-assembling peptide that may be preferably used in the present invention, there is given a peptide having an amino acid sequence represented by the following formula (I):

$$a_1b_1c_1b_2a_2b_3db_4a_3b_6c_2b_6a_4 \qquad (I)$$

where: $a_1$ to $a_4$ each represent a basic amino acid residue; $b_1$ to $b_6$ each represent a non-charged polar amino acid residue and/or a hydrophobic amino acid residue, provided that at least five thereof each represent a hydrophobic amino acid residue; $c_1$ and $c_2$ each represent an acidic amino acid residue; and d represents a hydrophobic amino acid residue.

In the amino acid sequence, $a_1$ to $a_4$ each represent a basic amino acid residue. The basic amino acid is preferably arginine, lysine, or histidine, more preferably arginine or lysine because those amino acids are highly basic. $a_1$ to $a_4$ may represent the same amino acid residue or different amino acid residues.

In the amino acid sequence, $b_1$ to $b_6$ each represent a non-charged polar amino acid residue and/or a hydrophobic amino acid residue, provided that at least five thereof each represent a hydrophobic amino acid residue. The hydrophobic amino acid is preferably alanine, leucine, isoleucine, valine, methionine, phenylalanine, tryptophan, glycine, or proline, and the non-charged polar amino acid is preferably tyrosine, serine, threonine, asparagine, glutamine, or cysteine, because those amino acids are easily available.

It is preferred that $b_3$ and $b_4$ each independently represent any appropriate hydrophobic amino acid residue. It is more preferred that $b_3$ and $b_4$ each independently represent a leucine residue, an alanine residue, a valine residue, or an isoleucine residue. It is particularly preferred that $b_3$ and $b_4$ each independently represent a leucine residue or an alanine residue.

It is preferred that all of $b_1$ to $b_6$ represent hydrophobic amino acid residues. This is because the self-assembling peptide can suitably form a β-sheet structure to self-assemble. It is more preferred that $b_1$ to $b_6$ each independently represent a leucine residue, an alanine residue, a valine residue, or an isoleucine residue. It is even more preferred that $b_1$ to $b_6$ each independently represent a leucine residue or an alanine residue. In a preferred embodiment, four or more of $b_1$ to $b_6$ represent leucine residues, it is more preferred that five or more of $b_1$ to $b_6$ represent leucine residues, and it is even more preferred that all of $b_1$ to $b_6$ represent leucine residues.

In the amino acid sequence, $c_1$ and $c_2$ each represent an acidic amino acid residue. The acidic amino acid is preferably aspartic acid or glutamic acid, because those amino acids are easily available. $c_1$ and $c_2$ may represent the same amino acid residue or different amino acid residues.

In the amino acid sequence, d represents a hydrophobic amino acid residue. d preferably represents an alanine residue, a valine residue, a leucine residue, or an isoleucine residue.

In one preferred embodiment, two of three continuous amino acid residues, $b_3$, d, and $b_4$, represent leucine residues and the remainder represents an alanine residue. In this case, any of $b_3$, d, and $b_4$ may represent an alanine residue. In addition, in another preferred embodiment, all of the three continuous amino acid residues, $b_3$, d, and $b_4$, represent leucine residues.

Preferred specific examples of the amino acid sequence represented by the formula (I) are listed below.

n-RLDLRLALRLDLR-c (SEQ ID NO: 1)

n-RLDLRLLLRLDLR-c (SEQ ID NO: 2)

n-RADLRLALRLDLR-c (SEQ ID NO: 3)

n-RLDLRLALRLDAR-c (SEQ ID NO: 4)

n-RADLRLLLRLDLR-c (SEQ ID NO: 5)

n-RADLRLLLRLDAR-c (SEQ ID NO: 6)

n-RLDLRALLRLDLR-c (SEQ ID NO: 7)

n-RLDLRLLARLDLR-c (SEQ ID NO: 8)

As another self-assembling peptide that may be preferably used in the present invention, there is given a peptide described in WO 2007/000979 A1, i.e., a self-assembling peptide including polar amino acid residues and non-polar amino acid residues (hydrophobic amino acid residues), in which the self-assembling peptide includes an acidic amino acid residue and a basic amino acid residue as the polar amino acid residues, a sum of charge of the acidic amino acid residue and charge of the basic amino acid residue in a neutral region is a number excluding 0, and the self-assembling peptide is capable of forming a β-sheet structure in which only the non-polar amino acid residue is arranged on one surface upon self-assembly in an aqueous solution.

Of the self-assembling peptides, a peptide including an acidic amino acid residue, a basic amino acid residue, and a non-charged polar amino acid as polar amino acids is preferred. Preferred specific examples of the self-assembling peptide are listed below.

n-RASARADARASARADA-c (SEQ ID NO: 9)

n-RANARADARANARADA-c (SEQ ID NO: 10)

n-RAAARADARAAARADA-c (SEQ ID NO: 11)

n-RASARADARADARASA-c (SEQ ID NO: 12)

n-RADARASARASARADA-c (SEQ ID NO: 13)

n-RASARASARASARADA-c (SEQ ID NO: 14)

n-RASARADARASA-c (SEQ ID NO: 15)

n-KASAKAEAKASAKAEA-c (SEQ ID NO: 16)

n-SAEAKAEASAEAKAEA-c (SEQ ID NO: 17)

n-KLSLKLDLKLSL-c (SEQ ID NO: 18)

n-KLALKLDLKLAL-c (SEQ ID NO: 19)

The self-assembling peptide may be produced by any appropriate production method. Examples thereof include a chemical synthetic method, such as a solid-phase method, for example, an Fmoc method or a liquid-phase method, and a molecular biological method, such as gene recombinant expression.

The self-assembling peptide may be subjected to any appropriate modification depending on a purpose or the like. A site at which the modification is performed is not particularly limited, and examples thereof include an N-terminal amino group and a C-terminal carboxyl group of a self-assembling peptide, and both of the groups.

Any appropriate modification may be selected as the modification as long as the peptide after the modification has a self-assembling ability. Examples thereof include: the introduction of a protective group, such as acetylation of the N-terminal amino group or amidation of the C-terminal carboxyl group; the introduction of a functional group, such as alkylation, esterification, or halogenation; hydrogenation; the introduction of a saccharide compound, such as a monosaccharide, a disaccharide, an oligosaccharide, or a polysaccharide; the introduction of a lipid compound, such as a fatty acid, a phospholipid, or a glycolipid; the introduction of an amino acid or a protein; the introduction of DNA; and the introduction of, for example, other compounds each having bioactivity. Only one kind of modification may be performed, or two or more kinds thereof may be performed in combination. For example, the following may be adopted: a desired amino acid is introduced into the C-terminal of the self-assembling peptide to yield an added peptide, the N-terminal of the added peptide is acetylated, and the C-terminal thereof is amidated.

When an amino acid or a protein is introduced, the number of the amino acids to be introduced is preferably from 1 to 180, more preferably from 1 to 50, even more preferably from 1 to 30, particularly preferably from 1 to 10, most preferably from 1 to 5. When the number of the amino acid residues to be introduced exceeds 180, the self-assembling ability may be impaired.

The bone formation promoter of the present invention may include only one kind of self-assembling peptide or two or more kinds of self-assembling peptides.

The concentration of the self-assembling peptide in the bone formation promoter of the present invention may be appropriately set depending on the composition, use application, or the like. The concentration of the self-assembling peptide is preferably from 0.1 wt % to 5.0 wt %, more preferably from 0.1 wt % to 3.0 wt %, even more preferably from 0.1 wt % to 2.0 wt %. When the concentration falls within the above-mentioned range, the effects of the present invention can be suitably obtained.

[A-2. Bone Chip]

The bone chip to be used in the present invention may be a bone of a patient himself/herself to be treated with the bone formation promoter of the present invention or a bone of another person. In addition, the bone chip may be a bone collected from a site to which the bone formation promoter is applied or a bone collected from another site. As a bone to be used as the bone chip, for example, a bone chip excised for decompression or the like may be used.

The collected bone chip may be used without additional treatment or after being subjected to any appropriate pretreatment. Examples of the pretreatment include washing by perfusion with phosphate buffered saline (PBS) and drying.

The size of the bone chip is not particularly limited, and may be any appropriate size depending on a site to which the bone formation promoter is applied. For example, the collected bone chip may be used without additional treatment, may be formed into a section having a desired thickness, or may be processed into a product having any appropriate size (for example, powder) before use. When the collected bone chip is applied without additional treatment, the size of the bone chip is, for example, from 0.5 mm to 5.0 mm, preferably from 1.0 mm to 4.0 mm. In addition, when the bone chip is processed into a product having any appropriate size (for example, powder) before use, the size of the bone chip is, for example, from 0.01 mm to 0.5 mm, preferably from 0.02 mm to 0.4 mm. The size of the bone chip is preferably from 0.03 mm to 0.3 mm, more preferably from 0.04 mm to 0.2 mm. When the size of the bone chip falls within the above-mentioned range, bone formation can be promoted more suitably. The term "size of the bone chip" as used herein refers to a size of the maximum part in one bone chip.

The bone chip may be processed into a product having a desired size by any appropriate means. An example thereof is a grinding mill.

The content of the bone chip in the bone formation promoter of the present invention is preferably from 1 part by weight to 100 parts by weight, more preferably from 1 part by weight to 90 parts by weight, with respect to 100 parts by weight of a self-assembling peptide gel. When the content of the bone chip falls within the above-mentioned range, bone formation can be promoted more suitably. The term "self-assembling peptide gel (used as a standard)" as used herein refers to a gel consisting only of the self-assembling peptide and water.

[A-3. Blood and Blood-derived Component]

The bone formation promoter of the present invention preferably further includes blood and/or a blood-derived component. When the bone formation promoter further includes blood and/or a blood-derived component, an effect of promoting induction of cartilage formation can be obtained. As the blood-derived component, there are given, for example, an erythrocyte, a leucocyte, a platelet, and plasma. The blood-derived components may be used alone or in combination.

The blood and/or blood-derived component may be collected from a patient or another person. In addition, there may be used a blood product, such as a whole blood product, an erythrocyte product, a platelet product, or a plasma product.

The concentration of the blood and/or blood-derived component in the bone formation promoter of the present invention is preferably from 0.001 ppm to 1,000 ppm, more preferably from 0.01 ppm to 1,000 ppm. When the concentration of the blood and/or blood-derived component falls within the above-mentioned range, bone formation can be promoted more suitably.

[A-4. Bone Morphogenetic Protein]

The bone formation promoter of the present invention preferably further includes a bone morphogenetic protein (BMP). When the bone formation promoter further includes the bone morphogenetic protein, the bone formation promoter of the present invention can further promote bone formation. Specific examples of the bone morphogenetic protein include: BMPs in the BMP2/4 group, such as BMP2 and BMP4; BMPs in the OP-1 group, such as BMP5, BMP6, BMP7, BMP8a, and BMP8b; BMPs in the BMP9 group, such as BMP9 and BMP10; and BMPs in the GDF5 group, such as GDF5, GDF6, and GDF7. The bone morphogenetic protein is preferably BMP-2 because bone formation can be suitably promoted. The bone morphogenetic protein may be appropriately modified as long as the bone morphogenetic protein after the modification has an effect of promoting bone formation almost equal to that of the bone morphogenetic protein. In addition, a human recombinant bone morphogenetic protein (rhBMP) may be used as the bone morphogenetic protein. The bone morphogenetic proteins may be used alone or in combination. The human BMPs have already been cloned, and hence may be obtained based on their base sequences by a genetic engineering technique.

The concentration of the bone morphogenetic protein in the bone formation promoter of the present invention is typically from 0.001 ppm to 1,000 ppm, preferably from 0.01 ppm to 1,000 ppm. When the concentration falls within such range, an effect of a bone morphogenetic protein can be suitably exhibited to promote bone formation.

[A-5. Other Physiologically Active Substances]

The bone formation promoter of the present invention may further include a physiologically active substance other than the above-mentioned bone morphogenetic proteins. As the physiologically active substance that may be included in the bone formation promoter of the present invention, there are given, for example: a differentiation control factor (for example, TGF-β) capable of inducing or promoting differentiation of bone or cartilage; growth hormone; a cell function control factor, such as EGF or FGF; and an immune- or inflammation-related factor, such as an interferon or an interleukin.

The concentration of the physiologically active substance in the bone formation promoter of the present invention is typically from 0.001 ppm to 1,000 ppm, preferably from 0.01 ppm to 1,000 ppm. When the concentration falls within such range, an effect of the physiologically active substance can be suitably exhibited to promote bone formation.

[A-6. Other Additives]

The bone formation promoter of the present invention may further include any appropriate additive, if necessary. Specific examples of the additive include: a pH adjuster; a buffer; a tonicity agent; a salt; an amino acid; a vitamin; an alcohol; a protein; and a drug. Such additives may be used alone or in combination.

Examples of the pH adjuster include hydrochloric acid, citric acid, acetic acid, sodium hydroxide, potassium hydroxide, sodium hydrogen carbonate, and sodium carbonate.

Examples of the buffer include: phosphoric acid and phosphates, such as sodium phosphate, sodium dihydrogen phosphate, disodium hydrogen phosphate, potassium phosphate, potassium dihydrogen phosphate, and dipotassium hydrogen phosphate; boric acid and borates, such as borax, sodium borate and potassium borate; citrates, such as sodium citrate and disodium citrate; acetates, such as sodium acetate and potassium acetate; Tris; and HEPES.

Examples of the tonicity agent include: chlorides, such as sodium chloride, potassium chloride, calcium chloride, and magnesium chloride; monosaccharides, such as glucose, fructose, and galactose; disaccharides, such as sucrose, trehalose, maltose, and lactose; and sugar alcohols, such as mannitol and sorbitol.

As the salt, there may be used any appropriate salt other than the additives listed above. Examples thereof include sodium sulfate and magnesium sulfate.

The addition amounts of the additives may be set to any appropriate values depending on a purpose or the like.

[B. Preparation Method]

The bone formation promoter of the present invention may be prepared by any appropriate method. The bone formation promoter may be prepared by, for example, mixing a self-assembling peptide, water, and any other component, leaving the mixture to stand to prepare a self-assembling peptide gel, and mixing the gel with a bone chip. The self-assembling peptide to be used in the present invention spontaneously assembles in a solution to form fibrous molecular assemblies through an interaction of the molecules. When the assemblies are further left to stand, a three-dimensional network structure is further developed by an interaction between the molecular assemblies to form a gel. The time and temperature at which the assemblies are left to stand may be appropriately set depending on a target of administration, the concentration and kind of the self-assembling peptide, and the like. As the water, purified water, such as ion-exchanged water or distilled water, may be preferably used.

When a small bone chip (for example, bone chip powder) is used as the bone chip, the self-assembling peptide gel is preferably mixed with the bone chip because the bone chip can be dispersed uniformly. Meanwhile, when a large bone chip (for example, a bone chip having a size of about 3 mm) is used as the bone chip, the self-assembling peptide gel may be mixed with the bone chip or may not be mixed with the bone chip (only the bone chip may be added to the gel). A method for the mixing is not particularly limited, and any appropriate mixing means may be adopted.

A method of preparing the bone formation promoter of the present invention may further include any appropriate steps such as: purification, such as filtration; sterilization, such as high-pressure steam sterilization, radiation sterilization, or dry-heat sterilization; and dispensing into a packaging container.

[C. Retainer for Bone Formation Promoter]

In one embodiment, the bone formation promoter of the present invention is used together with a retainer for a bone formation promoter. The bone formation promoter has adequate strength at a neutral pH similar to that of a body environment. When the bone formation promoter is fixed by the retainer of the present invention, the bone formation promoter can be retained at an administration site. This can promote bone formation at an administration site of interest, and can promote, for example, bone fusion.

The retainer for a bone formation promoter is preferably a net or an instrument having a network structure. The retainer of the present invention having such form can retain the bone formation promoter without applying an excessive burden to an administration site. Accordingly, the retainer can be used without applying a burden to the bone of an aged person who has reduced bone strength. In addition, it has been difficult to fix a fractured bone at a site having a complex shape. However, the retainer for a bone formation promoter of the present invention may be a net, and hence can fit even a site having a complex shape. Thus, the retainer can retain the bone formation promoter well. As the instrument having a network structure, for example, a stent is given.

The retainer for a bone formation promoter of the present invention is preferably formed of a carbon-based material because the material has high biological safety. Any appropriate material may be used as the carbon-based material. Examples of the carbon-based material include a carbon-based fiber and a carbon nanotube. As the carbon-based material, a carbon-based fiber and a carbon nanotube are preferred.

In addition, any appropriate orthopedic implant product may be used as the retainer for a bone formation promoter. Specific examples thereof include a cage, a screw, and a rod.

The orthopedic implant product may be formed of any appropriate material. Examples thereof include: metals, such as pure titanium, a titanium alloy, a titanium-nickel alloy, and cobalt-chromium; polycarbonate resins; polyacetal resins; polyester resins, such as polyethylene terephthalate, polybutylene terephthalate, and polycyclohexylene dimethyl terephthalate; polyphenylene ether resins; polyphenylene oxide; polyamide resins, such as nylon 6, nylon 66, and aromatic polyamide; syndiotactic polystyrene; engineering resins, such as ultra-high-molecular-weight polyethylene; and super engineering resins, such as a polyphenylene sulfide resin, a polysulfone resin, a polyether sulfone resin, a polyether ether ketone resin, a polyarylate resin, a liquid crystal polymer, an aromatic polyester resin, a polyimide resin, a polyamide imide resin, a polyether imide resin, and an aramid resin. Orthopedic implant products made of an engineering resin or a super engineering resin are preferably used because the products are excellent in heat resistance, mechanical strength, chemical resistance, and abrasion resistance. In addition, the engineering resin or the super engineering resin may contain a reinforcing material, such as carbon fiber.

[D. Use Method for Bone Formation Promoter]

In one embodiment, the bone formation promoter of the present invention may be administered in a gel form, and a small bone chip (for example, bone chip powder) may be suitably used. Accordingly, the bone formation promoter can be easily administered by a syringe or the like and can be filled in a complex or narrow administration site (for example, a gap of a cracked bone).

In another embodiment, the bone formation promoter of the present invention is used by being gelated and administered to (injected into) an administration site. When the bone formation promoter is gelated, a state in which the bone chip is dispersed well in the bone formation promoter can be maintained. Accordingly, the bone formation promoter of the present invention can suitably exhibit an effect of promoting bone formation.

Injection of the bone formation promoter into the administration site may be performed by any appropriate means, such as a syringe, a tube, or a pipette.

The self-assembling peptide included in the bone formation promoter of the present invention is excellent in biodegradability. In addition, the bone chip included in the bone formation promoter of the present invention facilitates bone formation and contributes to new bone formation. The bone chip included in the bone formation promoter of the present invention may remain at the administration site even after degradation of the self-assembling peptide to become a part of a fused bone.

Further, in another embodiment, the bone formation promoter of the present invention is used together with the retainer for a bone formation promoter. For example, a gel-like bone formation promoter is administered to an administration site, and then the administration site and the bone formation promoter may be covered with a retainer for a bone formation promoter having a net shape to retain the bone formation promoter. Alternatively, the retainer for a bone formation promoter (for example, a cage) may be filled with the bone formation promoter and then attached to an administration site. In addition, for example, a gel-like bone formation promoter may be administered to an administration site after the retainer for a bone formation promoter (for example, a stent) is applied in advance to the administration site. In this embodiment, the bone formation promoter and the retainer may be integrated with each other. However, the self-assembling peptide included in the bone formation promoter of the present invention is excellent in biodegradability, and hence is absorbed and decomposed with time, and the bone chip may become apart of a fused bone.

Accordingly, after completion of bone formation, only the retainer for a bone formation promoter may be removed, if necessary.

The bone formation promoter of the present invention may be used in combination with any appropriate fixation means, if necessary. For example, the spine is a site to which a large load is always applied, and hence it is necessary to fix the bone formation promoter more stably. Accordingly, for example, when the bone formation promoter of the present invention is applied to a fractured spine, the bone formation promoter of the present invention may be used in combination with conventional fixation means, such as a plate or a screw, to promote bone formation in a stably fixed state and to promote bone fusion in a more appropriate state.

The bone formation promoter of the present invention may be used for, for example, repair of a defect site in a bone tissue, a periodontal tissue, or the like. In addition, the bone formation promoter of the present invention can promote bone formation while reducing the burden on the bone. Accordingly, the bone formation promoter of the present invention can be suitably applied to an aged person who may have reduced bone strength and reduced bone regeneration function.

EXAMPLES

Now, the present invention is specifically described on the basis of Examples, but the present invention is not limited by these Examples.

Test Example 1: Cell Culture Test

50 µl of a self-assembling peptide gel 1 (manufactured by Menicon Co., Ltd., trade name: Panacea Gel SPG-178-208 (a peptide gel including a peptide represented by SEQ ID NO: 1 (SPG-178) and having an acetylated N-terminal and an amidated C-terminal (the sum of charges of amino acid residues constituting the self-assembling peptide in a neutral region (pH 7.0): +2), the concentration of the peptide: 0.8 w/w %) was left to stand at 4° C. for 1.5 hours. Subsequently, 500 µl of a medium (obtained by adding 10% fetal bovine serum (FBS) and 1% penicillin-streptomycin (Pen-Strep) solution to MEMα) was added thereto, and the whole was left to stand at 37° C. for 1 hour. Then, the medium was exchanged, and the resultant was added to a 24-well plate. MC3T3-E1 cells were inoculated into the 24-well plate at 50,000 cells/well and cultured at room temperature for 24 hours, and the medium was exchanged for a differentiation induction medium (obtained by further adding 1% ascorbic acid, 0.2% hydrocortisone, and 2% β-glycerophosphate to the above-mentioned medium), followed by culture of the cells at room temperature. Meanwhile, for comparison, the cells were cultured in the same manner as above except that a self-assembling peptide gel C1 (manufactured by 3-D Matrix, Ltd., trade name "PuraMatrix™", a gel having a concentration of a peptide represented by Ac-RADARA-DARADARADA-CONH$_2$ (SEQ ID NO: 20) of 1 wt %) was used instead of the self-assembling peptide gel 1. Further, only the cells were cultured in the same manner as above except that the self-assembling peptide gel was not added. On day 1, day 7, day 14, and day 28 of culture, the cells were subjected to ALP staining and RNA extraction. The expression levels of RNAs were measured by RT-PCR. The alkaline phosphatase (ALP) staining was performed by the following method.

(ALP Staining)

A staining treatment was performed using a Histofine SAB-PO® kit (manufactured by Nichirei Biosciences Inc.). The medium was aspirated from the wells, and the wells were washed three times with phosphate buffered saline (PBS). Subsequently, the cells were fixed with 4% paraformaldehyde (PFA), left to stand for 10 minutes, and washed three times with PBS. After that, the cells were subjected to permeabilization treatment with a 0.2% Triton X (trademark)-PBS solution, left to stand for 10 minutes, and washed three times with PBS. A blocking reagent I (3% hydrogen peroxide in methanol) was added thereto, and the cells were left to stand for from 10 minutes to 15 minutes and washed three times with PBS. After that, a blocking reagent II (10% goat normal serum) was added thereto, and the cells were left to stand for 10 minutes. Then, a primary antibody (ALP antibody: abcam anti-alkaline phosphatase, tissue non-specific [EPR4477] antibody ab 108337) was added thereto, and the cells were left to stand for 2 hours and washed three times with PBS. Subsequently, a secondary antibody (a biotin-labeled anti-rabbit IgG antibody) was added thereto, and the cells were left to stand for 10 minutes and washed three times with PBS. Subsequently, an enzyme reagent (peroxidase-labeled streptavidin) was added thereto, and the cells were left to stand for 5 minutes and washed three times with PBS. After that, a substrate solution (DAB substrate kit: a solution obtained by adding two drops (about 40 μl) of a chromogenic substrate (reagent A) and two drops (about 40 μl) of a substrate buffer (reagent B) to 1 ml of purified water, mixing the resultant without forming bubbles, adding one drop (about 40 μl) of a chromogenic reagent (reagent C) thereto, and mixing the resultant without forming bubbles) was added thereto, and the cells were left to stand for from 5 minutes to 20 minutes and washed three times with purified water. Subsequently, the cells were counterstained (hematoxylin), left to stand for 2 minutes, subjected to color formation with water, left to stand for 10 minutes, and observed with a microscope.

<Results>

Microphotographs of the cells on day 0, day 1, day 7, day 14, and day 28 of culture and photographs of the cells subjected to ALP staining are shown in FIG. 1A to FIG. 1D. According to ALP staining, ALP serving as a bone formation marker is stained. When the self-assembling peptide gel 1 was used, ALP staining positive osteoblasts aggregated, indicating that bone formation was able to be induced sufficiently (FIG. 1). Meanwhile, when only the cells were cultured, ALP expression detected by ALP staining was observed at a low level because the cells were not differentiated. When the self-assembling peptide gel C1 was used, the ranges of the ALP staining positive cells were detected (FIG. 1).

Figure 2:
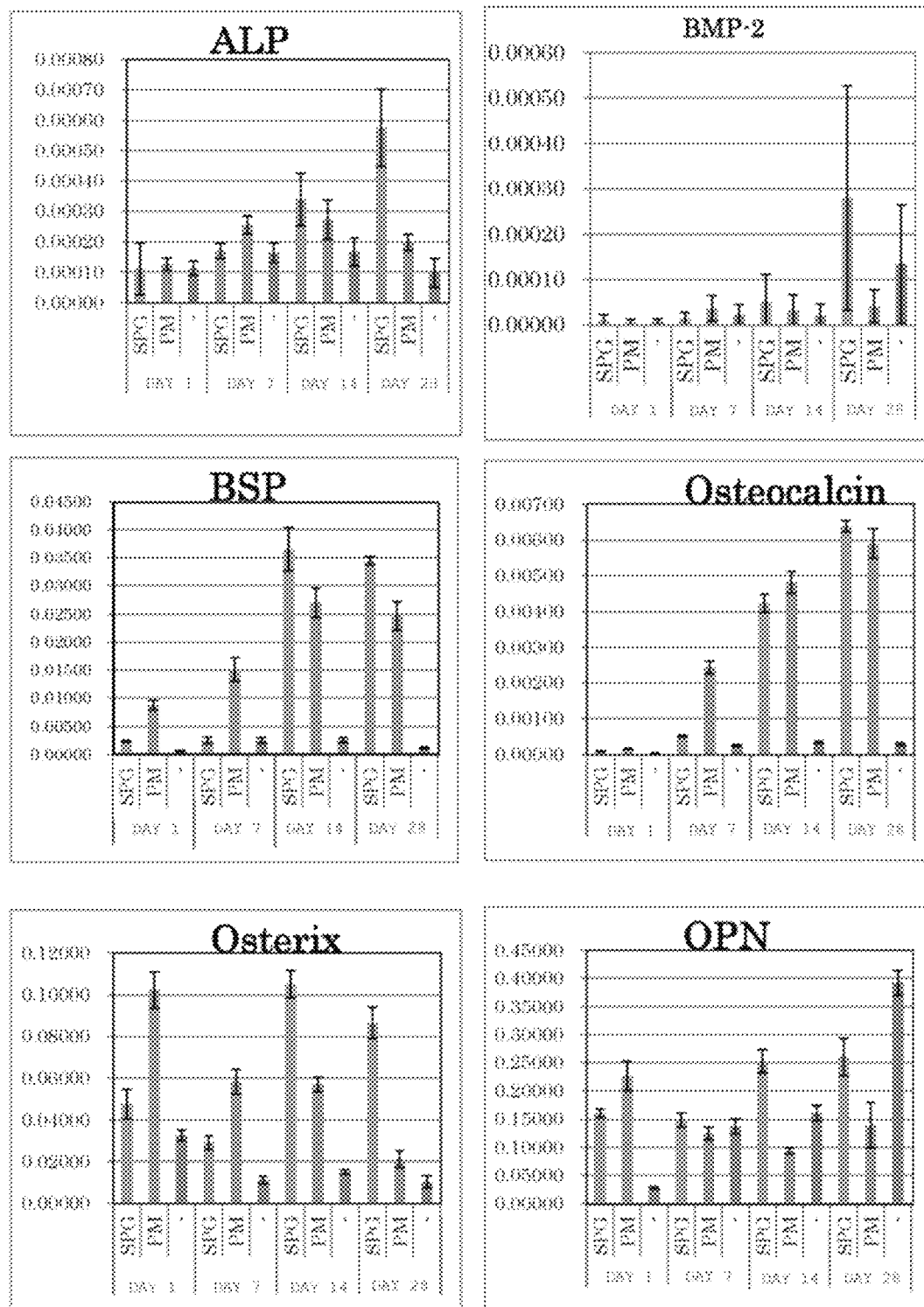
FIG. 2 shows graphs for showing expression levels of bone formation markers in cells on day 1, day 7, day 14, and day 28 of culture.

Graphs for showing expression levels of bone formation markers (ALP, BMP-2, bone sialoprotein (BSP), osteocalcin, osterix, and osteopontin (OSP)) in the cells on day 1, day 7, day 14, and day 28 of culture are shown in FIG. 2. When the self-assembling peptide gel 1 (SPG in FIG. 2) was used, the expression levels of ALP, BMP-2, OPN, BSP, and osterix significantly increased on day 28 of culture (bone formation mature period) as compared to culture of the cells using the self-assembling peptide gel C1 (PM in FIG. 2). In general, ALP is a marker that is expressed at an increased level at an early stage of bone formation. The expression level of ALP was high like the other bone formation markers, and hence the use of the self-assembling peptide gel 1 was considered to sustainably induce the bone formation markers.

Example 1

The femur of a mouse was pulverized using a pulverizer to produce bone chips (1 mm to 2 mm). A self-assembling peptide gel 2 (manufactured by Menicon Co., Ltd., trade name: Panacea Gel SPG-178-204, the concentration of a peptide: 0.4 w/w %) was placed on the resultant bone chips, and the whole was left to stand to produce a gel-like bone formation promoter 1. The composition of the self-assembling peptide gel 2 is shown in Table 1.

Figure 3:
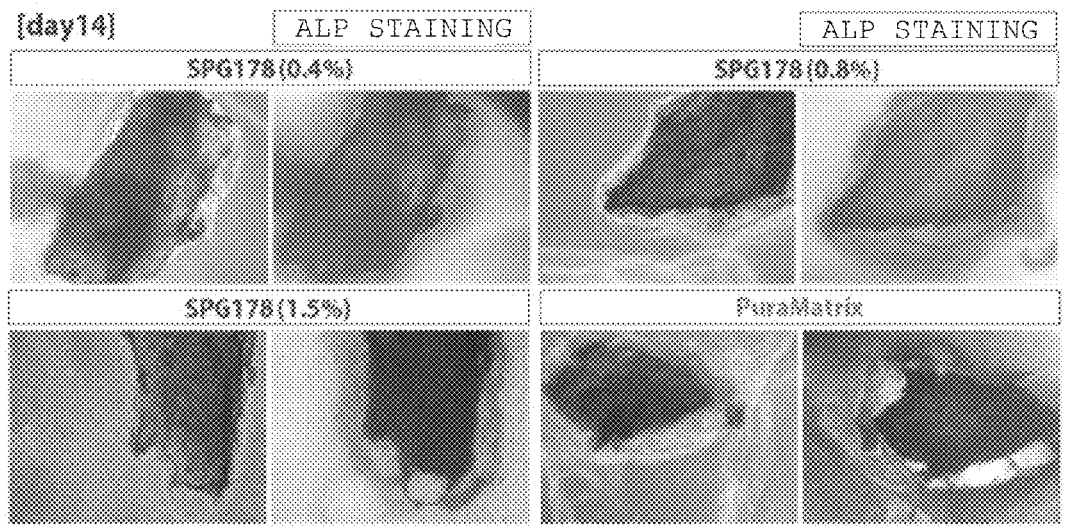
FIG. 3 shows photographs of bone formation promoters of Examples 1 to 3 and a bone formation promoter of Comparative Example 1 on day 14 and day 28 of culture and photographs of the promoters subjected to ALP staining.
Figure 3:
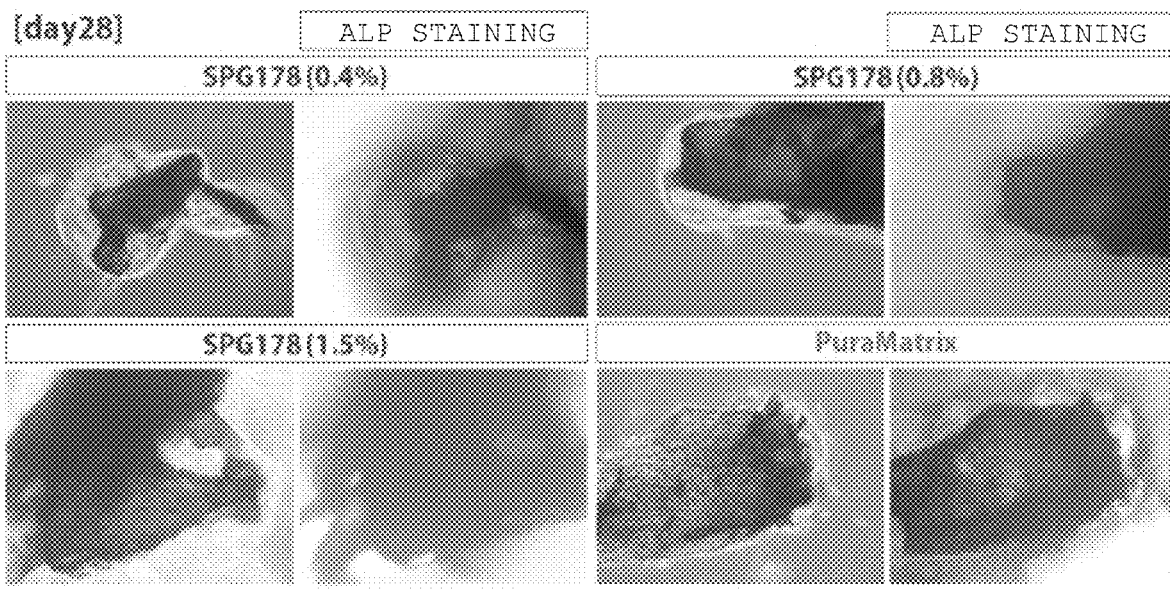

The resultant bone formation promoter was cultured using a medium MEMα, 10% FBS, and 1% Anti-Anti. Photographs of the bone formation promoters on day 14 and day 28 of culture and photographs of the bone formation promoters subjected to ALP staining are shown in FIG. 3.

TABLE 1

| | Amino acid sequence of self-assembling peptide | Sum of charges at neutral pH | Concentration of peptide (w/w %) | pH adjuster | pH* | Tonicity agent | Concentration of tonicity agent (w/w %) |
|---|---|---|---|---|---|---|---|
| Self-assembling peptide gel 1 | Ac-RLDLRLALRLDLR-NH$_2$ (SEQ ID NO: 1) (N-terminal: Acetylated, C-terminal: Amidated) | +2 | 0.8 | Sodium carbonate | 6 | Trehalose dihydrate | 8.5 |
| Self-assembling peptide gel 2 | Ac-RLDLRLALRLDLR-NH$_2$ (SEQ ID NO: 1) (N-terminal: Acetylated, C-terminal: Amidated) | +2 | 0.4 | Sodium carbonate | 6 | Trehalose dihydrate | 8.5 |
| Self-assembling peptide gel 3 | Ac-RLDLRLALRLDLR-NH$_2$ (SEQ ID NO: 1) (N-terminal: Acetylated, C-terminal: Amidated) | +2 | 1.5 | Sodium carbonate | 6 | Trehalose dihydrate | 8.5 |
| Self-assembling peptide gel 4 | Ac-KLSLKLDLKLSL-NH$_2$ (SEQ ID NO: 18) (N-terminal: Acetylated, C-terminal: Amidated) | +2 | 1.5 | Sodium carbonate | 7 | Trehalose dihydrate | 7.9 |
| Self-assembling peptide gel C1 | Ac-RADARADARADARADA-NH$_2$ (SEQ ID NO: 20) (N-terminal: Acetylated, C-terminal: Amidated) | 0 | 1.0 | — | 3 | — | — |

*: pH in production

Example 2

A bone formation promoter 2 was obtained in the same manner as in Example 1 except that a self-assembling peptide gel 1 was used instead of the self-assembling peptide gel 2. The resultant bone formation promoter 2 was cultured in the same manner as in Example 1. Photographs of the bone formation promoters on day 14 and day 28 of culture and photographs of the bone formation promoters subjected to ALP staining are shown in FIG. 3.

Example 3

A bone formation promoter 3 was obtained in the same manner as in Example 1 except that a self-assembling peptide gel 3 was used instead of the self-assembling peptide gel 2. The composition of the self-assembling peptide gel 3 is shown in Table 1. The resultant bone formation promoter 3 was cultured in the same manner as in Example 1. Photographs of the bone formation promoters on day 14 and day 28 of culture and photographs of the bone formation promoters subjected to ALP staining are shown in FIG. 3.

Comparative Example 1

A bone formation promoter C1 was obtained in the same manner as in Example 1 except that a self-assembling peptide gel C1 (manufactured by 3-D Matrix, Ltd., trade name "PuraMatrix™", a gel having a concentration of a peptide represented by Ac-RADARADARADARADA-CONH$_2$ (SEQ ID NO: 20) of 1 wt %) was used instead of the self-assembling peptide gel 2. The composition of the self-assembling peptide gel C1 is shown in Table 1. The resultant was cultured in the same manner as in Example 1 except that the resultant bone formation promoter C1 was used. Photographs of the bone formation promoters on day 14 and day 28 of culture and photographs of the bone formation promoters subjected to ALP staining are shown in FIG. 3.

(Results)
In the bone formation promoters 1 to 3, ALP staining positive osteoblasts were observed. Meanwhile, in the bone formation promoter C1, the bone chips were sequestrated, and no osteoblasts were observed.

Example 4

A bone defect site with a size of 1 mm×3 mm was made on the femur of a mouse using a drill to prepare a femur defect mouse.

The bone formation promoter 1 obtained in Example 1 was transplanted into the femur defect site of the resultant femur defect mouse. The femur site of the mouse was incised on day 2, day 7, day 9, day 14, and day 21 of transplantation to observe bone formation. In the mouse transplanted with the bone formation promoter 1, bone fusion at the defect site progressed. The bone formation promoter 1 of the present invention was found to obviously promote bone formation as compared to typical progression of bone fusion.

[Test Example 2] Femur Regeneration Test

A femur regeneration test was performed using a femur defect mouse by the following procedure. The femur regeneration ability was evaluated by performing X-ray imaging and CT imaging for a femur defect site on day 56 of external fixation. Conditions of the X-ray imaging and CT imaging are described below. In addition, bone regeneration rates were calculated from the results of the CT imaging. The test was performed using four mice for each bone formation promoter.

Figure 4:
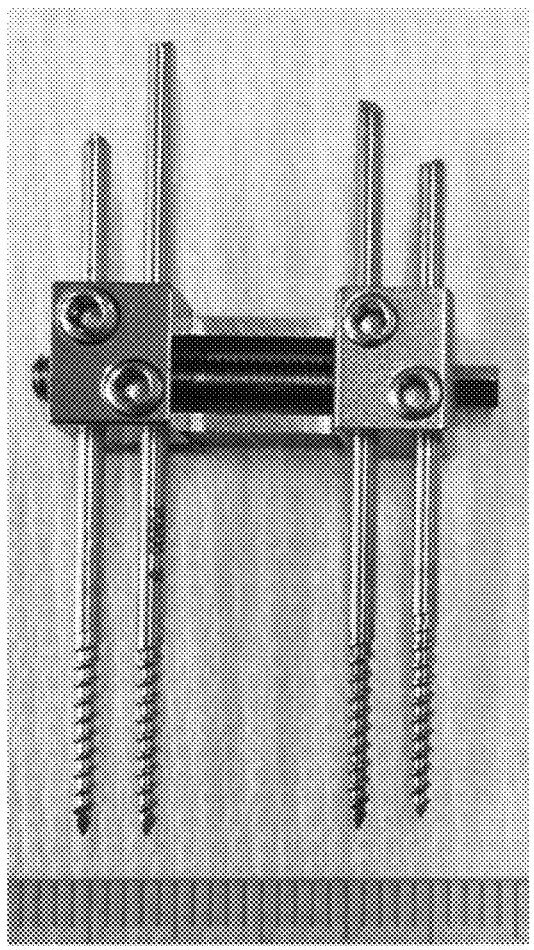
FIG. 4 shows a photograph of an external fixator used in preparation of a femur defect model.

(1) Preparation of Femur Defect Model 0.1 ml to 0.15 ml of Somnopentyl (manufactured by Kyoritsu Seiyaku Corporation) was injected intraperitoneally to each of 10-week-old female rats (purchased from Chubu Kagaku Shizai Co., Ltd.) for anesthesia, and the thigh was incised to put an external fixator (FIG. 4) on the femur. Subsequently, the femur at the middle point of the site on which the external fixator was put was shaved using an airtome to form a bone defect site with a size of about 5 mm.

(2) Preparation of Bone Chip

The femur collected from the rat was shaved using the airtome to collect a bone chip. The collected bone chip was stored at −80° C. until use.

(3) Preparation of Bone Formation Promoter 0.05 g of the bone chip was mixed with 80 µL of a self-assembling peptide gel 1 (manufactured by Menicon Co., Ltd., trade name: Panacea Gel SPG-178-208, the concentration of the peptide: 0.8 w/w %) to produce a bone formation promoter. A bone formation promoter was obtained in the same manner except that the self-assembling peptide gel C1 (manufactured by 3-D Matrix, Ltd., trade name "PuraMatrix™") or physiological saline was used instead of the self-assembling peptide gel 1.

(4) External Fixation at Femur Defect Site

Figure 5:
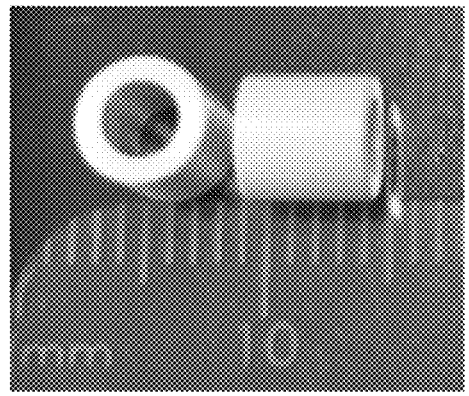
FIG. 5 shows a photograph of a cage used in preparation of a femur defect model.
Figure 6:
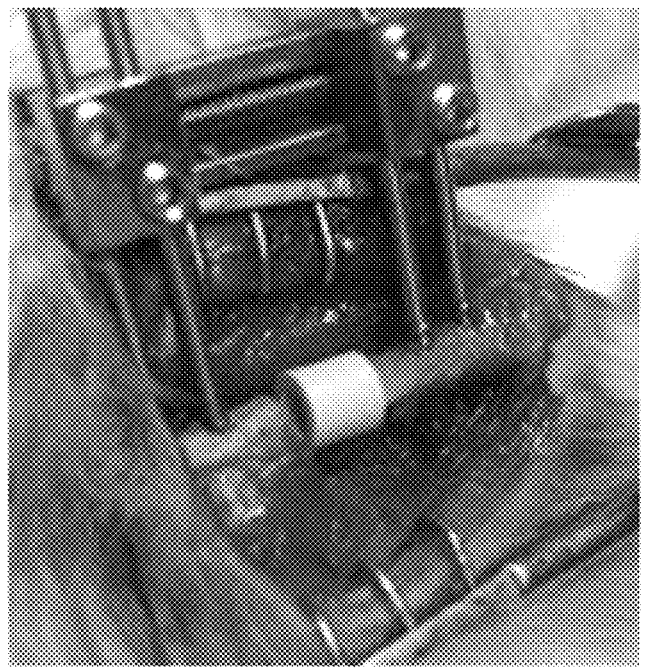
FIG. 6 shows a photograph of a mouse femur subjected to external fixation.

Each of the bone formation promoters prepared in the step (3) above was injected into a cage made of PEEK (manufactured by Yasojima Proceed Co., Ltd., length: 5 mm, outer diameter: 5 mm, inner diameter: 3 mm, FIG. 5). Subsequently, the cage including the bone formation promoter injected was inserted into the femur defect site of the femur defect mouse, and external fixation was performed as shown in FIG. 6.

<X-Ray Imaging>
X-ray imaging device: SOFTEX CMB-2 (manufactured by Softex Co., Ltd.)
(Imaging Conditions)
Voltage: 50 KVp
Current: 10 mA
Time: 15 sec
Imaging distance: 60 cm
Film: Fujifilm Corporation
<CT Imaging>
CT imaging device: high resolution in vivo micro X-ray CT scanner (SKYSCAN 1176)
(Imaging Conditions)
Filter: Cu+AL
Source voltage: 80 KV
Source current: 313 µA
Number of rows: 1,336
Number of columns: 2,000
Image pixel size: 17.6 µm
(Reconstruction Conditions)
Reconstruction program: NRecon
Pixel size: 17.60223 µm
Minimum for CS to image conversion: 0.002
Maximum for CS to image conversion: 0.03
<Calculation Method for Bone Regeneration Rate>
A bone shape analysis was performed using numerical analysis software "CTAn" manufactured by SKYSCAN to determine a bone regeneration rate.

(Results)

X-ray images and CT images of the femur defect sites subjected to the external fixation using the bone formation promoters are shown in FIG. 7 and FIG. 8, respectively. In the mice each having a femur defect site to which the bone formation promoter including the self-assembling peptide 1 was applied, bone regeneration was observed at the whole defect sites (SPG-178 in FIG. 7 and FIG. 8). In addition, in all the mice, the bone regeneration rates were 50% or more (the average of the bone regeneration rates: 66.68%, p=0.01). Meanwhile, in the mice to which the bone formation promoter including the self-assembling peptide C1 was applied, bone regeneration was observed only at the both sides of the femurs (PuraMatrix in FIG. 7 and FIG. 8). In addition, the bone regeneration rates were lower than those of the mice to which the bone formation promoter including the self-assembling peptide 1 was applied (the average of bone regeneration rates: 31.54%, p=0.01). Further, the bone regeneration rates were lower than those of the mice to which physiological saline was applied as a control (the average of bone regeneration rates: 44.18%, p=0.01). In addition, the bone regeneration rates of the mice to which the bone formation promoter including the self-assembling peptide 1 was applied was significantly higher than those of the mice to which the bone formation promoter including the self-assembling peptide C1 was applied.

Example 5

A self-assembling peptide gel 3 was diluted with Milli-Q water to prepare a 1.0 w/w % aqueous solution of the self-assembling peptide gel 3. The resultant aqueous solution was added dropwise to a 24-well plate, and properties of the gel were observed with a stereomicroscope (magnification: 100 times). In addition, the pH of the gel was measured with pH test paper.

5 mg of the bone chip (rat femur) obtained in Test Example 2 above was placed in a test tube, and 5 µL of the resultant aqueous solution was added dropwise thereto. Subsequently, the resultant was stirred with a vortex mixer, and then air bubbles were removed with a centrifugal separator to prepare a bone formation promoter 5. The properties of the resultant bone formation promoter 5 were observed with a stereomicroscope (magnification: 100 times). In addition, the pH of the resultant bone formation promoter was measured with pH test paper.

Example 6

A bone formation promoter 6 was obtained in the same manner as in Example 5 except that a self-assembling peptide gel 4 was used. The composition of the self-assembling peptide gel 4 is shown in Table 1. The properties and pH of the gel before addition of the bone chip and the properties and pH of the bone formation promoter 6 were evaluated in the same manner as in Example 5.

Comparative Example 2

A bone formation promoter C2 was obtained in the same manner as in Example 5 except that a self-assembling peptide gel C1 was used. The properties and pH of the gel before addition of the bone chip and the properties and pH of the bone formation promoter C2 were evaluated in the same manner as in Example 5.

[Evaluation]

Figure 9:
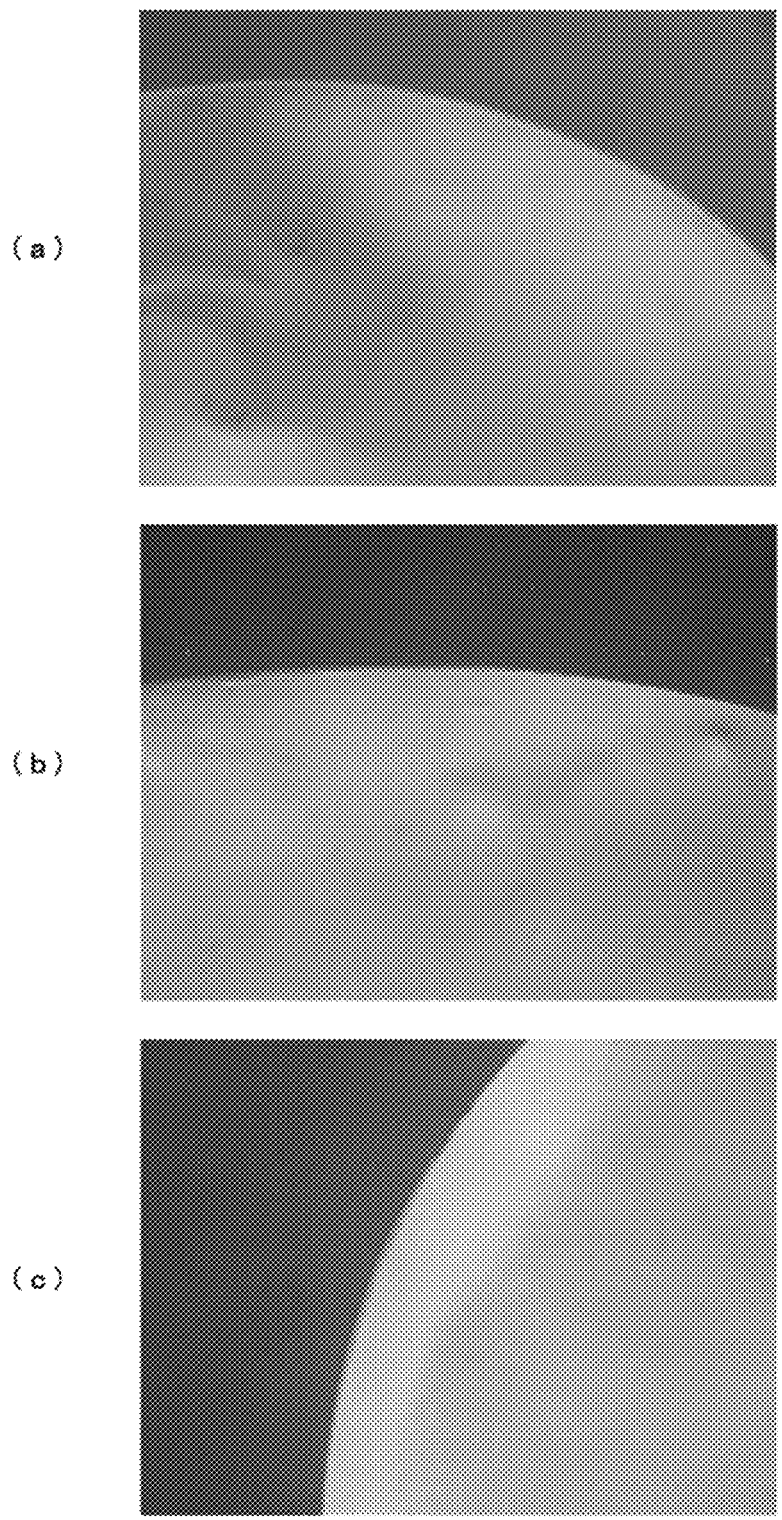
FIG. 9(a) shows a photograph of a gel before addition of a bone chip of Example 5.
FIG. 9(b) shows a photograph of a gel before addition of a bone chip of Example 6.
FIG. 9(c) shows a photograph of a gel before addition of a bone chip of Comparative Example 2.
Figure 10:
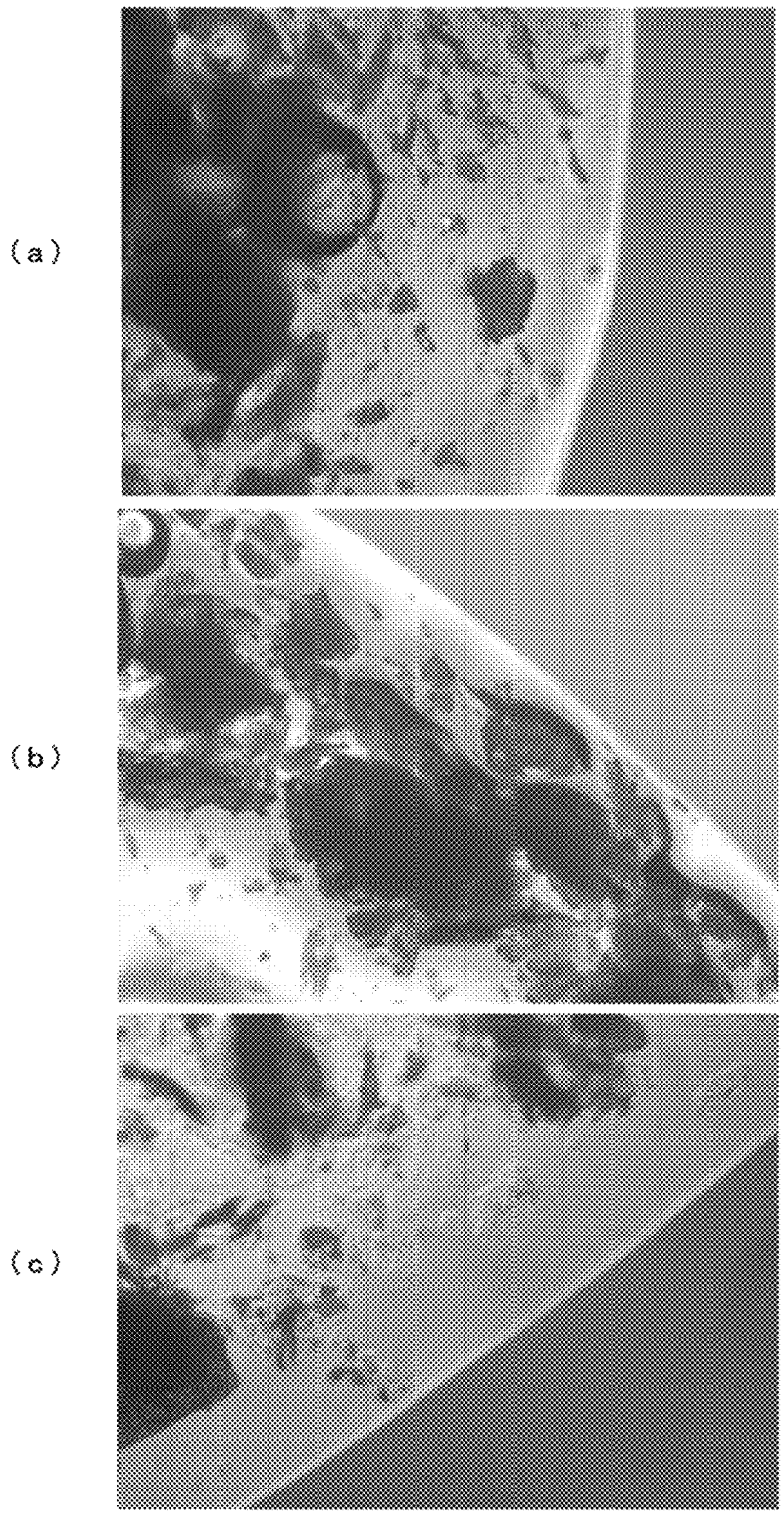
FIG. 10(a) shows a photograph of a gel (bone formation promoter) after addition of a bone chip of Example 5.
FIG. 10(b) shows a photograph of a gel (bone formation promoter) after addition of a bone chip of Example 6.
FIG. 10(c) shows a photograph of a gel (bone formation promoter) after addition of a bone chip of Comparative Example 2.

Photographs of the gels of Examples 5 and 6 and Comparative Example 2 before addition of the bone chip and photographs of the gels (bone formation promoters) after addition of the bone chip are shown in FIG. 9 and FIG. 10, respectively. As shown in FIG. 9, all the gels before addition of the bone chip were homogeneous gels. Observation of the bone formation promoters of Examples 5 and 6 with a stereomicroscope revealed that the bone chip were homogeneously dispersed in both of the bone formation promoters (FIG. 10(a) and FIG. 10(b)). Meanwhile, in the case of the bone formation promoter of Comparative Example 2, gel-like precipitates were detected, and the promoter was in a heterogeneous state (FIG. 10(c)).

In addition, in Examples 5 and 6, the pHs of the gels were neutral (about pH 6 to about pH 8) before and after addition of the bone chip. Meanwhile, in Comparative Example 2, the pH of the gel was acidic (about pH 4) before addition of the bone chip, and became neutral (about pH 6 to about pH 8) after addition of the bone chip.

In Examples 5 and 6, the pHs of the gels were maintained before and after addition of the bone chip, and hence the resultant bone formation promoters maintained uniform properties. It is considered that, in those examples, the bone chip was homogeneously dispersed, and hence the bone formation promoters served as scaffolds to improve bone formation rates. Meanwhile, it is considered that, in Comparative Example 2, the gel could not promote bone formation sufficiently because the gel became heterogeneous due to a change in pH by addition of the bone chip.

INDUSTRIAL APPLICABILITY

The bone formation promoter of the present invention can be suitably used for research and development or in the field of medicine.

The invention claimed is:

1. A bone formation promoter, comprising:
   a self-assembling peptide capable of forming a β-sheet structure in an aqueous solution having a neutral pH; and
   a bone chip,
   a sum of charges of amino acid residues constituting the self-assembling peptide at pH 7.0 being unequal to 0.
   wherein the self-assembling peptide is at least one peptide selected from the group consisting of SEQ ID NO: 1 to SEQ ID NO: 8, or is at least one peptide selected from the group consisting of SEQ ID NO: 1 to SEQ ID NO: 8 wherein a protective group has been introduced to their N-terminus and C-terminus.

2. The bone formation promoter according to claim 1, further comprising blood and/or a blood-derived component.

3. The bone formation promoter according to claim 1, further comprising a bone morphogenetic protein.

4. The bone formation promoter according to claim 1, wherein the bone formation promoter is used together with a retainer for a bone formation promoter.

5. A retainer comprising the bone formation promoter of claim 1.

6. The retainer for the bone formation promoter according to claim 5, wherein the retainer is formed of a carbon-based material, an engineering resin, or a super engineering resin.

7. The bone formation promoter according to claim 1, wherein the self-assembling peptide is SEQ ID NO: 1.

* * * * *

UNITED STATES PATENT AND TRADEMARK OFFICE
CERTIFICATE OF CORRECTION

PATENT NO. : 10,821,136 B2
APPLICATION NO. : 15/317569
DATED : November 3, 2020
INVENTOR(S) : Kei Ando et al.

Page 1 of 1

It is certified that error appears in the above-identified patent and that said Letters Patent is hereby corrected as shown below:

On the Title Page

Item (71), should read:
NATIONAL UNIVERSITY CORPORATION TOKAI NATIONAL HIGHER EDUCATION AND RESEARCH SYSTEM, Nagoya (JP); MENICON CO., LTD., Nagoya-shi, Aichi (JP)

In the Claims

Column 25, Claim 1, Line 35, change "0." to --0,--.

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 20

<210> SEQ ID NO 1
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 1

Arg Leu Asp Leu Arg Leu Ala Leu Arg Leu Asp Leu Arg
1               5                   10

-continued

<210> SEQ ID NO 2
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 2

Arg Leu Asp Leu Arg Leu Leu Leu Arg Leu Asp Leu Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 3

Arg Ala Asp Leu Arg Leu Ala Leu Arg Leu Asp Leu Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 4

Arg Leu Asp Leu Arg Leu Ala Leu Arg Leu Asp Ala Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 5

Arg Ala Asp Leu Arg Leu Leu Leu Arg Leu Asp Leu Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 6

Arg Ala Asp Leu Arg Leu Leu Leu Arg Leu Asp Ala Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 7

Arg Leu Asp Leu Arg Ala Leu Leu Arg Leu Asp Leu Arg
1               5                   10

<210> SEQ ID NO 8
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 8

Arg Leu Asp Leu Arg Leu Leu Ala Arg Leu Asp Leu Arg
1               5                   10

<210> SEQ ID NO 9
<211> LENGTH: 16
<212> TYPE: PRT
<213> ORGANISM: Artificial Sequence
<220> FEATURE:
<223> OTHER INFORMATION: a self-assembling peptide that can be used in
      the present invention

<400> SEQUENCE: 9

Arg Ala Ser Ala Arg Ala Asp Ala Arg Ala Ser Ala Arg Ala Asp Ala
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: a self-assembling peptide that can be used in
      the present invention

<400> SEQUENCE: 10

Arg Ala Asn Ala Arg Ala Asp Ala Arg Ala Asn Ala Arg Ala Asp Ala
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: a self-assembling peptide that can be used in
      the present invention

<400> SEQUENCE: 11

Arg Ala Ala Ala Arg Ala Asp Ala Arg Ala Ala Ala Arg Ala Asp Ala
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: a self-assembling peptide that can be used in
      the present invention

<400> SEQUENCE: 12

Arg Ala Ser Ala Arg Ala Asp Ala Arg Ala Asp Ala Arg Ala Ser Ala
1               5                   10                  15

<210> SEQ ID NO 13
<211> LENGTH: 16

```
<212> TYPE: PRT
<213> ORGANISM: Artificial Sequence
<220> FEATURE:
<223> OTHER INFORMATION: a self-assembling peptide that can be used in
      the present invention

<400> SEQUENCE: 13

Arg Ala Asp Ala Arg Ala Ser Ala Arg Ala Ser Ala Arg Ala Asp Ala
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: a self-assembling peptide that can be used in
      the present invention

<400> SEQUENCE: 14

Arg Ala Ser Ala Arg Ala Ser Ala Arg Ala Ser Ala Arg Ala Asp Ala
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: a self-assembling peptide that can be used in
      the present invention

<400> SEQUENCE: 15

Arg Ala Ser Ala Arg Ala Asp Ala Arg Ala Ser Ala
1               5                   10

<210> SEQ ID NO 16
<211> LENGTH: 16
<212> TYPE: PRT
<213> ORGANISM: Artificial Sequence
<220> FEATURE:
<223> OTHER INFORMATION: a self-assembling peptide that can be used in
      the present invention

<400> SEQUENCE: 16

Lys Ala Ser Ala Lys Ala Glu Ala Lys Ala Ser Ala Lys Ala Glu Ala
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: a self-assembling peptide that can be used in
      the present invention

<400> SEQUENCE: 17

Ser Ala Glu Ala Lys Ala Glu Ala Ser Ala Glu Ala Lys Ala Glu Ala
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: a self-assembling peptide that can be used in
      the present invention

<400> SEQUENCE: 18

Lys Leu Ser Leu Lys Leu Asp Leu Lys Leu Ser Leu
```

-continued

```
<210> SEQ ID NO 19
<211> LENGTH: 12
<212> TYPE: PRT
<213> ORGANISM: Artificial Sequence
<220> FEATURE:
<223> OTHER INFORMATION: a self-assembling peptide that can be used in
      the present invention

<400> SEQUENCE: 19

Lys Leu Ala Leu Lys Leu Asp Leu Lys Leu Ala Leu
1               5                   10

<210> SEQ ID NO 20
<211> LENGTH: 16
<212> TYPE: PRT
<213> ORGANISM: Artificial Sequence
<220> FEATURE:
<223> OTHER INFORMATION: comparaitive sequence

<400> SEQUENCE: 20

Arg Ala Asp Ala Arg Ala Asp Ala Arg Ala Asp Ala Arg Ala Asp Ala
1               5                   10                  15
```